(12) United States Patent
Fukuda

(10) Patent No.: US 10,619,178 B2
(45) Date of Patent: Apr. 14, 2020

(54) BIOSENSOR AND PRODUCTION METHOD FOR SAME

(71) Applicant: ARKRAY, Inc., Kyoto (JP)

(72) Inventor: Kazuo Fukuda, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 197 days.

(21) Appl. No.: 15/689,792

(22) Filed: Aug. 29, 2017

(65) Prior Publication Data

US 2018/0057851 A1    Mar. 1, 2018

(30) Foreign Application Priority Data

Aug. 30, 2016   (JP) ................. 2016-167810

(51) Int. Cl.

| | |
|---|---|
| *A61B 5/00* | (2006.01) |
| *C12Q 1/00* | (2006.01) |
| *G01N 33/543* | (2006.01) |
| *G01N 27/327* | (2006.01) |
| *A61B 5/145* | (2006.01) |
| *B01D 59/50* | (2006.01) |
| *C02F 1/469* | (2006.01) |
| *G01N 27/30* | (2006.01) |
| *B01D 61/00* | (2006.01) |

(52) U.S. Cl.
CPC .......... *C12Q 1/006* (2013.01); *A61B 5/14532* (2013.01); *B01D 59/50* (2013.01); *C02F 1/469* (2013.01); *C12Q 1/004* (2013.01); *G01N 27/307* (2013.01); *G01N 27/3272* (2013.01); *G01N 33/5438* (2013.01); *B01D 61/00* (2013.01); *B01L 2300/0645* (2013.01)

(58) Field of Classification Search
CPC ..... A61B 5/14532; B01D 59/50; C02F 1/469; C12Q 1/004; C12Q 1/006
See application file for complete search history.

(56) References Cited

U.S. PATENT DOCUMENTS

| | | | | |
|---|---|---|---|---|
| 6,287,451 | B1 * | 9/2001 | Winarta | C12Q 1/002 204/403.03 |
| 6,863,800 | B2 * | 3/2005 | Karinka | G01N 27/3272 204/403.11 |
| 9,014,774 | B2 * | 4/2015 | Mao | A61B 5/14532 600/347 |
| 9,237,865 | B2 * | 1/2016 | Wang | A61B 5/14532 |
| 9,476,849 | B2 * | 10/2016 | Uchiyama | G01N 27/3274 |
| 2004/0040839 | A1 | 3/2004 | Yagi | |

(Continued)

FOREIGN PATENT DOCUMENTS

| | | |
|---|---|---|
| EP | 1717319 A2 | 11/2006 |
| JP | H02-221855 A | 9/1990 |

(Continued)

OTHER PUBLICATIONS

Extended European Search Report issued in corresponding European Patent Application No. 17188635.1 dated Nov. 27, 2017.

(Continued)

*Primary Examiner* — Max F Hindenburg
(74) *Attorney, Agent, or Firm* — Morgan, Lewis & Bockius LLP

(57) ABSTRACT

The disclosure relates to a biosensor including electrodes, a hydrophilic region or layer, and a reagent layer that contains an enzyme and a mediator, and methods of producing thereof.

19 Claims, 16 Drawing Sheets

(56) References Cited

U.S. PATENT DOCUMENTS

| | | | |
|---|---|---|---|
| 2005/0230252 A1* | 10/2005 | Tsai | C12Q 1/006 204/450 |
| 2006/0246214 A1 | 11/2006 | Plotkin et al. | |
| 2007/0287191 A1 | 12/2007 | Stiene et al. | |
| 2009/0057146 A1 | 3/2009 | Teodorczyk et al. | |
| 2011/0297555 A1 | 12/2011 | Stiene et al. | |
| 2012/0181184 A1 | 7/2012 | Whitesides et al. | |
| 2014/0262773 A1 | 9/2014 | Riggles et al. | |
| 2015/0369770 A1 | 12/2015 | Inose et al. | |

FOREIGN PATENT DOCUMENTS

| | | |
|---|---|---|
| JP | 2000-121593 A | 4/2000 |
| JP | 2003-185618 A | 7/2003 |
| JP | 2006-308596 A | 11/2006 |
| JP | 2009-063577 A | 3/2009 |
| JP | 2015-200570 A | 11/2015 |
| JP | 2016-510118 A | 4/2016 |
| WO | 02/35222 A1 | 5/2002 |
| WO | 2006/015615 A1 | 2/2006 |
| WO | 2010/102279 A1 | 9/2010 |

OTHER PUBLICATIONS

Office Action issued in corresponding Japanese Patent Application No. 2016-167810 dated Jan. 7, 2020.

* cited by examiner

Comparative Example 1 (in which a hydrophilic region is not formed)

Example 1 (in which the hydrophilic region is formed))

θ=83.6°
(NO SURFACE
TREATMENT)

θ=50.3°
($\Delta$θ=42.7°)

θ=73.3°
($\Delta$θ=10.3°)

θ=31.5°
($\Delta$θ=52.5°)

θ=63.7°
($\Delta$θ=19.9°)

θ=21.2°
($\Delta$θ=62.3°)

θ=60.4°
($\Delta$θ=23.2°)

BIOSENSOR AND PRODUCTION METHOD FOR SAME

CROSS-REFERENCE TO RELATED APPLICATION

This application claims the benefit of Japanese Patent Application No. 2016-167810 filed on Aug. 30, 2016 in the Japanese Patent Office, the disclosure of which is herein incorporated in its entirety by reference.

FIELD

The present disclosure relates to a biosensor and a production method for the same.

BACKGROUND

In a conventional biosensor, a reagent layer containing at least an oxidoreductase and an electron transfer mediator (also referred to as "mediator," "electron transfer substance," or "electron carrier") is disposed on two or more electrodes formed on an insulation substrate.

In a biosensor of this type, exchange of electrons is performed between substance to be measured and oxidoreductase, and the electrons then move via the electron transfer mediator to the electrode, allowing the measurement of the current value.

Examples of the aforementioned biosensor include a biosensor in which a reagent layer containing glucose dehydrogenase as an enzyme and potassium ferricyanide as an electron carrier is formed on a counter electrode, a measurement electrode, and a detection electrode.

In this biosensor, the reagent layer is dissolved into blood having been sucked into a specimen supply path, and an enzyme reaction proceeds with glucose which is a substrate in the blood.

Then, the electron carrier is reduced, and thereby, a reduced-type electron carrier is formed. When the reduced-type electron carrier is electrochemically oxidized, this causes an electric current, and the glucose concentration in the blood is measured based on the value of the current thus obtained.

SUMMARY

In a biosensor using a reagent layer containing an electron transfer mediator, a sample may introduced into a capillary, and a reagent layer disposed in the capillary may be dissolved by the sample. An oxidation-reduction reaction may then be generated, and current (i.e., Cottrell current) generated at the time of the oxidation-reduction reaction may be measured. Accordingly, the sensitivity of such a biosensor depends on the contact area between the sample in which the reagent layer is dissolved and the working electrode that exchanges electrons with the sample. A variation in the contact area between a sample and a working electrode may cause variation in sensitivity among biosensors.

In the biosensor produced by the methods described herein, the area ratios of reagent covering the working electrode and the counter electrode may not vary significantly (e.g. within 10, 5, 3 or 1% or less) due to the reduced positional deviation and/or due to lack of masks during the production of the biosensor. Thus, the sensitivities may not be varied among the batches of biosensors produced.

Also in the biosensor described herein, the working electrode may not be completely surrounded by the counter electrode, and/or the entire working electrode and the counter electrode may not be covered with the reagent. If the working electrode is surrounded by the counter electrode, and the entire working electrode and counter electrode are covered with the reagent, a design restriction of, for example, covering a reagent region which overlaps with a lead section, with an insulation material becomes a problem.

In the biosensor described herein, the working electrode has a neighboring region without an counter electrode, and/or the working electrode or the counter electrode is only partially covered with the reagent.

The biosensor and a production method for the same disclosed herein would reduce a production cost and variation in sensitivity among the produced biosensors.

In some embodiments, a biosensor includes (a) electrodes that are formed on an insulation substrate, the electrodes including a working electrode and a counter electrode disposed side by side in a first direction such that one of the working electrode and the counter electrode is sandwiched by the other; (b) a hydrophilic region that is continuously formed on the electrodes, the hydrophilic region (i) having higher hydrophilicity than a surrounding region thereof, (ii) comprising first ends, in a second direction orthogonal to the first direction, disposed between both ends of the working electrode and between both ends of the counter electrode, and (iii) comprising second ends, in the first direction, disposed on one of the working electrode and the counter electrode disposed on the outermost side (e.g., a pair of working electrodes or a pair of counter electrodes, which are disposed on the outermost side); and (c) a reagent layer comprising an enzyme and a mediator, the reagent layer being disposed on the hydrophilic region. In some embodiments, the reagent layer is not disposed on any other regions outside of the hydrophilic region. In additional embodiments, at least 80%, 85%, 90%, 91%, 92%, 93%, 94%, 95%, 96%, 97%, 99% or 100% of the surface of the reagent layer facing the hydrophilic region is in direct contact with the hydrophilic region.

In additional embodiments, the reagent layer is formed in a rectangular shape. However, the regent layer may be formed in a circle or an elliptic. Further, in the biosensor according to some embodiments, a space between one of the counter electrodes and the working electrode, which are disposed on the outermost side, is substantially the same as a space between the other counter electrode and the working electrode, which correspond to the one of the counter electrodes and the working electrode Moreover, in the biosensor according to additional embodiments, the working electrode and the counter electrode are disposed in parallel with each other.

The disclosure is also related to a production method for a biosensor. The method includes (i) forming, on an insulation substrate, electrodes including a working electrode and a counter electrode arranged side by side in a first direction such that at least a part of the working electrode or the counter electrode is sandwiched by the other, (ii) forming a hydrophilic region that is continuously formed on the electrodes, the hydrophilic region having higher hydrophilicity than a surrounding region thereof, comprising first ends, in a second direction orthogonal to the first direction, disposed between both ends of the working electrode and between both ends of the counter electrode, and comprising second ends, in the first direction, disposed on one of the working electrode and the counter electrode disposed on the outermost side (e.g., a pair of working electrodes or a pair of counter electrodes, which are disposed on the outermost side), (iii) supplying, to the hydrophilic region, a reagent liquid containing an enzyme and a mediator, and (iv) forming a reagent layer through solidification of the reagent liquid.

DESCRIPTION OF EMBODIMENTS

Figure 1:
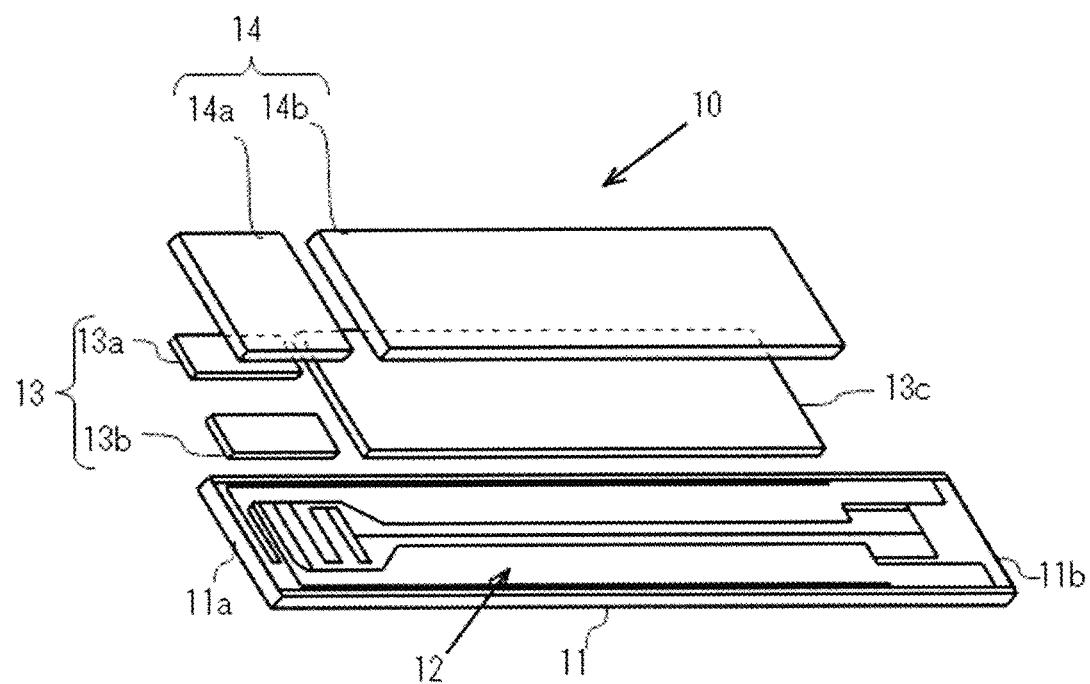
FIG. 1 is an exploded perspective view of a biosensor according to an embodiment.

Hereinafter, a biosensor and a production method for the same according to some embodiments of the present invention are described with reference to the drawings. The configuration of an embodiment described below is an example, and the present invention is not limited to the configuration of the embodiments below.

A production method for a biosensor according to some embodiments includes: (1) forming a working electrode and a counter electrode disposed side by side in a first direction on an insulation substrate such that (a) one of the working electrode and the counter electrode is sandwiched by the other; (2) forming a continuous hydrophilic region or layer on the electrodes, the continuous hydrophilic region or layer having higher hydrophilicity compared to the surrounding region thereof, comprising first ends, in a second direction orthogonal to the first direction, disposed between both ends of the working electrode and between both ends of the counter electrode, and comprising second ends, in the first direction, disposed on one of the working electrode and the counter electrode disposed on the outermost side (e.g., a pair of working electrodes or a pair of counter electrodes, which are disposed on the outermost side); (3) supplying a reagent liquid containing an enzyme and a mediator to the hydrophilic region; and (4) forming a reagent layer through solidification of the reagent liquid. Here, a "continuous" hydrophilic region or layer refers to a region or layer having a continuous hydrophilic surface without gaps or divisions that are not hydrophilic. In some embodiment, 5, 4, 3, 2 or 1 hydrophilic regions or layers are formed on at least one of the working electrode or counter electrode or on the group of electrodes in a biosensor described herein. In additional embodiment, only a single continuous hydrophilic region or layer is formed on at least one of the working electrode or counter electrode or on the group of electrodes in a biosensor described herein.

According to the production method, the reagent liquid is dropped or dispensed onto the hydrophilic region or layer, such that the reagent liquid may be spread over the hydrophilic region or layer based on the hydrophilicity of the hydrophilic region or layer. Here, the hydrophilicity of the region or layer surrounding the hydrophilic region or layer on the surface where the reagent liquid is applied is lower than that of the hydrophilic region, and thus, spreading of the reagent liquid is restricted or suppressed. Accordingly, the reagent liquid may be solidified in a state where the reagent liquid has been spread over a desired range (e.g., the entire hydrophilic region). For example, the reagent liquid does not spread to a region that is not the hydrophilic region or layer. In other words, the hydrophilic region is prepared selectively in a desired range in a part including the working electrode and the counter electrode, and accordingly, the reagent layer may be formed such that a desired area of the reagent layer is in contact with the electrodes, or the reagent layer is in contact with the electrodes while being in a desired state.

In addition, according to the aforementioned production method, even when the position of the reagent layer formed on the hydrophilic region is deviated in an upper, lower, left, or right direction on the surface of the electrode, variation in ratio between the contact area between the working electrode and the reagent layer, and the contact area between the counter electrode and the reagent layer may be reduced.

Accordingly, the contact areas of the reagent layer with respect to the working electrode and the counter electrode may be made stable, and thus, variation in sensitivity among individual biosensors may be reduced. Furthermore, the accuracy (e.g., alignment accuracy) of the formation position of the hydrophilic region may be relaxed. Accordingly, the cost for producing the biosensor may be reduced.

The substance to be measured by the biosensor according to the embodiment is not particularly limited as long as it may be measured with use of the biosensor. However, the substance to be measured may be a substance from a living body or may serve as an index or control for a disease or health condition. The substance to be measured may be glucose (e.g., blood sugar) or cholesterol, for example. The sample is not particularly limited as long as it contains the substance to be measured. The sample may be a biological sample. Examples of the biological sample include blood and urine. Further, examples of the substance to be measured may include alcohol, sarcosine, fructosyl amine, pyruvic acid, lactic acid, and hydroxybutyric acid.

[Structure of Biosensor and Production Method for Biosensor]

Figure 2:
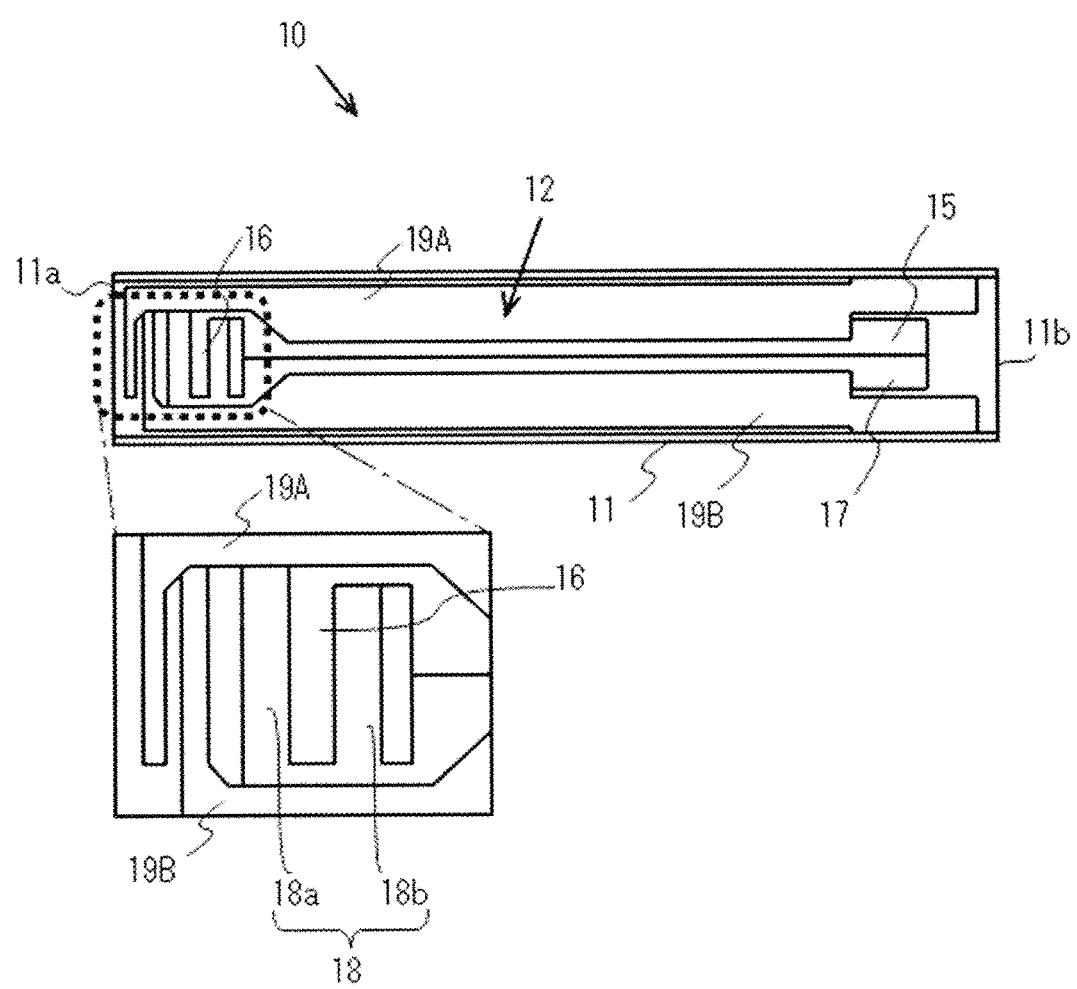
FIG. 2 illustrates an example of an electrode layer (an electrode pattern) formed on an insulation substrate illustrated in FIG. 1.

FIG. 1 is an exploded perspective view of a biosensor according to some embodiments. FIG. 2 illustrates an example of an electrode layer (i.e., an electrode pattern) 12 formed on an insulation substrate illustrated in FIG. 1.

In FIG. 1, a biosensor 10 includes an insulation substrate 11; an electrode layer 12 formed on one surface of the insulation substrate 11; spacers 13 (a spacer 13a and a spacer 13b); and a reinforcing material 13c which are stacked on the electrode layer 12; a cover 14a stacked on the spacer 13a and the spacer 13b, and a cover 14b stacked on the reinforcing material 13c. The biosensor 10 is formed by stacking the insulation substrate 11 having the electrode layer 12 formed thereon, the spacers 13 and the reinforcing material 13c, and the cover 14a and the cover 14b to be integrated with one another. The combination of the insulation substrate 11 and the electrode layer 12 may be referred to as "base material."

The insulation substrate 11 is formed into a flat plate shape or a band shape having one end 11a and the other end 11b in the longitudinal direction thereof. The insulation substrate 11 is formed from an insulation material. Examples of the insulation material include resin (e.g., plastic), glass, ceramics, paper, and rubber. As the plastic, various types of exemplary resins, such as polyetherimide (PEI), polyethylene terephthalate (PET), polyethylene (PE), polystyrene (PS), polymethacrylate (PMMA), polypropylene (PP), polyimide resin, acrylic resin, epoxy resin, and glass epoxy may be adopted. In addition to the plastic, photosensitive material, paper, glass, ceramics, biodegradable material, or the like also may be adopted as the insulation material. The longitudinal direction of the insulation substrate 11 corresponds to the longitudinal direction of the biosensor 10. Hereinafter, the longitudinal direction of the biosensor 10 is referred to as "first direction," and the width direction of the insulation substrate 11 or the biosensor 10, the width direction being orthogonal to the longitudinal direction, is referred to as "second direction."

The electrode layer 12 may be formed by using metal material, for example. Examples of the metal material include gold, platinum, silver, copper, palladium, iridium, ruthenium, aluminum, nickel, titanium, indium tin oxide (ITO), and zinc oxide (ZnO). In addition to the metal material, for example, carbon (graphite) may be used as the electrode material.

The electrode layer 12 has a desired thickness (for example, 10 μm, 100 nm, 90 nm, 80 nm, 70 nm, 60 nm or smaller) and has a predetermined electrode pattern. The electrode layer 12 is formed by plating a thin film of the electrode material, or by forming a film of the electrode material through physical vapor deposition (PVD, for example, spattering) or chemical vapor deposition (CVD). The electrode pattern is formed by excavating the metal film with laser beams or by etching the metal film by means of a mask. Alternatively, the electrode layer 12 may be formed by printing (for example, screen printing) of carbon material (for example, carbon ink).

As illustrated in FIG. 2, in order to measure glucose which is an example of the substance to be measured, the electrode layer 12 includes a working electrode 16 having a lead section 15 and a counter electrode 18 having a lead section 17. The counter electrode 18 includes a counter electrode 18a and a counter electrode 18b that are disposed in parallel with (with equal distance from) the working electrode 16 via spaces, gaps or grooves interposed therebetween. The electrode layer 12 further includes an electrode section 19A and an electrode section 19B to be used for a purpose other than measurement of glucose. The electrode section 19A and the electrode section 19B may be omitted. Hereinafter, the description is given on the assumption that the electrode section 19A and the electrode section 19B are not included.

In the example of FIG. 2, a two-electrode structure including the working electrode 16 and the counter electrode 18 for measurement of glucose is illustrated. In some embodiments, the present disclosure is also related to a biosensor having a three-electrode structure formed of a working electrode, a counter electrode, and a reference electrode for measurement of glucose. The reference electrode is formed by using silver/silver chloride (Ag/AgCl), for example.

In the biosensor 10 according to some embodiments, a hydrophilic region having higher hydrophilicity than the surrounding region thereof is prepared in a part including the working electrode 16 and the counter electrode 18, on the surface of the insulation substrate 11 on which the electrode layer 12 is formed. The hydrophilic region is continuously formed on the working electrode 16 and the counter electrodes 18a and 18b, has higher hydrophilicity than the surrounding region thereof. The hydrophilic region has first ends, in a second direction (e.g., width direction of the insulation substrate) orthogonal to the first direction (e.g., longitudinal direction of the insulation substrate), disposed between both ends of the working electrode 16 and between both ends, in the second direction, of the counter electrodes 18a and 18b. Further, the hydrophilic region has second ends, in the first direction, disposed on each of the counter electrode 18a and 18b which are disposed on the outermost side in the first direction (an example of "a pair of working electrodes or a pair of counter electrodes, which are disposed on the outermost side"). Such an amount of a liquid reagent-layer material (hereinafter, also referred to as "reagent liquid") as to spread to the boundary between the hydrophilic region and the surrounding region of the hydrophilic region, is supplied to the hydrophilic region. The solidified reagent-layer material is solidified on the hydrophilic region, whereby a reagent layer is formed. As shown in FIGS. 3A to 3D, the hydrophilic region hydrophilic region covers at least a part of the working electrode and at last two separate parts of the counter electrode.

Figure 3A:
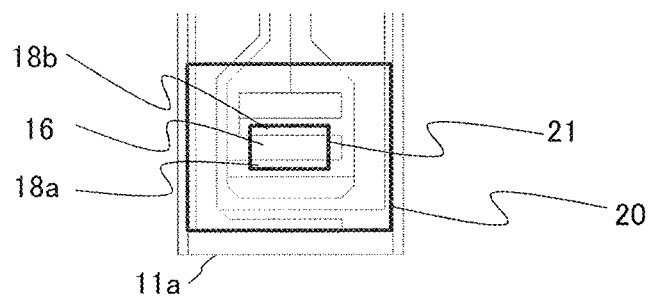
FIGS. 3A to 3D illustrate a production method for the biosensor, wherein an example of a method for forming a hydrophilic region and a reagent layer is illustrated.

FIGS. 3A to 3D illustrate an example of a method for forming a hydrophilic region and a reagent layer. As illustrated in FIG. 3A, a mask 20 is disposed on one surface of the insulation substrate 11 on which the electrode layer 12 is formed. In one example, the mask 20 is provided so as to cover the entire end 11a (e.g., the entire electrode at end 11a) of the insulation substrate 11.

The mask 20 has an opening 21 from which a first region above the working electrode 16 and a second region that is not above the working electrode 16 are exposed. In the example illustrated in FIGS. 3A to 3D, the opening 21 is provided from which the working electrode 16, the two counter electrodes 18a, 18b, and the surface of the insulation substrate 11 among the electrodes are exposed. As a material for the mask 20, a low adhesive sheet (low adhesive tape), a metal mask, a rubber plate, or the like may be used.

The size of the opening 21 may be determined in view of the contact area between the working electrode and the reagent layer, and/or the contact area between the reagent layer and the counter electrode, for example. The opening 21 has a rectangular shape in the example illustrated in FIGS. 3A to 3D, but may have a shape such as a circle, an ellipse, a triangle, or a polygon having five or more corners, other than a rectangular shape.

As illustrated in FIG. 2, when the working electrode and the counter electrode are formed of the band-like working electrode 16 and the two band-like counter electrodes 18a and 18b respectively disposed on both sides of the working electrode 16 in parallel with each other, the shape of the opening 21 may be a rectangular shape. The rectangular opening 21 may be formed such that the working electrode 16 and the counter electrodes 18a and 18b are exposed in the longitudinal direction (the direction of the one end 11a—the other end 11b) of the insulation substrate 11.

Figure 13:
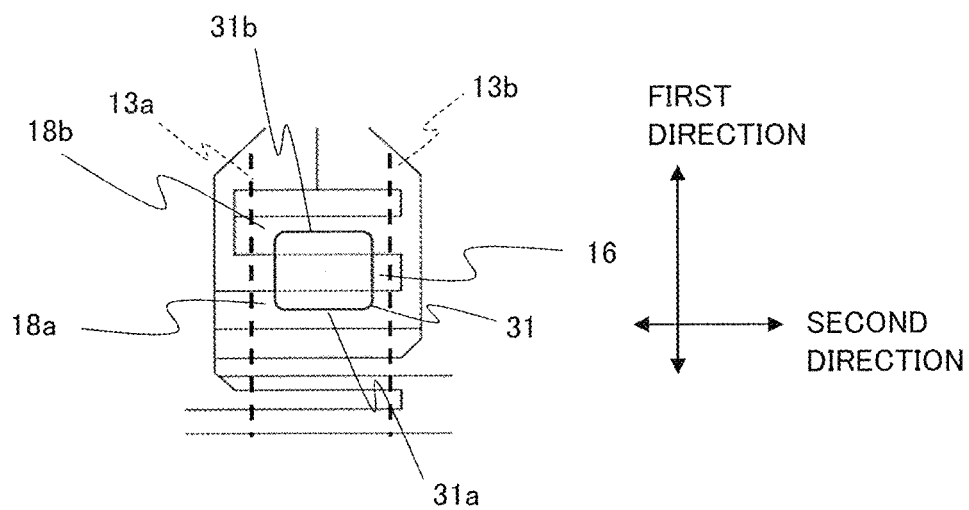
FIG. 13 is a diagram of the electrode section and the hydrophilic region of the biosensor.

In this case, even if the opening 21 is slightly deviated in the longitudinal direction of the insulation substrate 11, the total area of the counter electrode 18 exposed from the opening 21 (e.g., the sum of the exposed area of the counter electrode 18a and the exposed area of the counter electrode 18b) may be made uniform. That is, variation in the contact area between the counter electrode 18 and a reagent layer 40 may be reduced as disclosed herein. As shown in FIG. 13, the distance (width of a gap) between the working electrode 18a and the counter electrode 16 in the first direction may be different from the distance (width of a gap) between the working electrode 18b and the counter electrode 16 or may be the same as the distance (width of the gap) between the working electrode 18b and the counter electrode 16. That is, in some embodiments, a distance (a space, e.g., a gap or groove) between each of the pair of working electrodes or each of the pair of counter electrodes, which are disposed on the outermost side, and working electrodes or counter electrodes facing each of the pair of working electrodes or the pair of counter electrodes is the same Since the distances are formed to be the same (substantially equal to each other), an influence caused by deviation of the hydrophilic region 31 may be suppressed (CV may be stabilized), compared to the case where the spaces are different from each other. In order to suppress variation in contact area of the reagent layer 40 with respect to the working electrode 16 and the counter electrode 18, the opening 21 does not include an end of, in the width direction of the insulation substrate 11, at least one of the working electrode and the counter electrode 18.

Figure 3B:
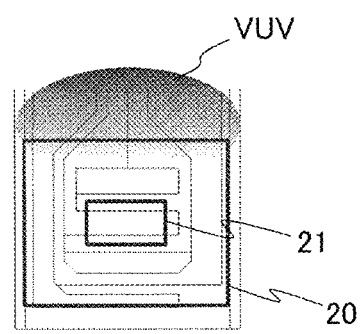
Figure 3C:
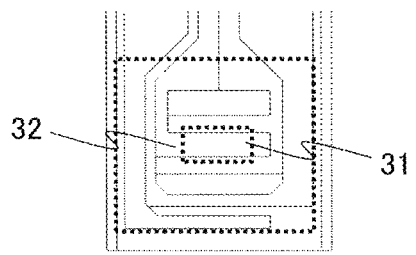
Figure 3D:
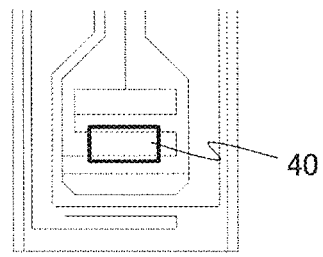

Next, as illustrated in FIG. 3B, the surface, of the electrode layer 12, exposed from the opening 21 is modified by irradiation with ultraviolet rays. The surface of the region exposed from the opening 21 is modified by irradiation with vacuum-ultraviolet (VUV) light, for example. Thus, the hydrophilicity (e.g, wettability) of the region is enhanced to be higher than that of the surrounding region which is covered with the mask 20.

After the mask 20 is removed, a region where the opening 21 existed (e.g., a region irradiated with ultraviolet rays) becomes the hydrophilic region 31 that has higher hydrophilicity than the surrounding region thereof. In this way, the hydrophilic region 31 is formed. The hydrophilic region 31 includes a first region formed on the working electrode 16 and a second region formed on a portion not on the working electrode 16. On the other hand, a region 32 which surrounds the hydrophilic region 31 and which is covered with the mask 20 becomes the region 32 (the surrounding region) that has lower hydrophilicity (higher water repellency) than the hydrophilic region 31 (see FIG. 3C). The area of the hydrophilic region 31 is defined. For example, the hydrophilic region 31 having the defined area is formed on the substrate by adjustment of the size of the opening 21. However, the production method for the hydrophilic region 31 having the defined area is not limited to size adjustment of the opening 21. Since the area of the hydrophilic region 31 is defined, the area of the reagent layer to be formed on the hydrophilic region 31 may be defined, and thus, the contact area between the working electrode and the reagent layer may be set to a desired area.

In the example of FIGS. 3A to 3D, the hydrophilic region 31 includes the first region and the second region which are continuous. The mask 20 having one opening 21 therein is used in order to form the hydrophilic region 31. However, the first region and the second region of the hydrophilic region 31 are not necessarily continuous (may be separated from each other). Thus, the number of the openings 21 for forming the first area and the second area may be two or greater. The hydrophilic region 31 may be formed by modification (e.g., hydrophilization) of the surface with plasma, instead of irradiation of the surface with ultraviolet rays. Alternatively, sandblasting of the surface may be performed as a method for forming the hydrophilic region 31.

Next, a predetermined amount of a liquid reagent-layer material (a reagent liquid) is dispensed (dropped) onto the hydrophilic region 31. Here, the reagent-layer material supplied to the hydrophilic region 31 spreads because the hydrophilicity has been improved by the surface modification. On the other hand, the region 32 surrounding the hydrophilic region 31 has lower hydrophilicity (e.g., higher water repellency) than the hydrophilic region 31, and thus, the dispersion range of the reagent liquid is reduced or limited to a range (e.g., within the hydrophilic region 31) that does not exceed the boundary between the hydrophilic region 31 and the surrounding region 32, by adjusting the supply amount of the reagent liquid, for example.

Further, the contact angle of the reagent liquid may be adjusted by adjusting the degree of surface modification in the hydrophilic region and the supply amount of the reagent liquid. In some embodiments, the supplied reagent spreads thinly over the entire hydrophilic region 31 because the reagent may be expected to be appropriately dispersed when a sample is introduced.

The dispersion range, the shape, and the area of the reagent liquid spared over the electrode layer 12 may be defined into desired ranges by adjusting the degree of surface modification in the hydrophilic region and the supply amount of the reagent liquid, as described above. Subsequently, the reagent-layer material is solidified through natural drying or heat drying. As a result of the solidification, a reagent layer 40 is formed on the hydrophilic region 31 (see FIG. 3D). That is, the reagent layer 40 is obtained of which the contact area with the electrodes (the working electrode 16 and the counter electrode 18) is defined (of which a predetermined area is in contact with the working electrode 16 and the counter electrode 18 by a predetermined area). In the embodiment, the reagent layer 40 is formed across the working electrode 16 and the counter electrode 18.

Figure 4:
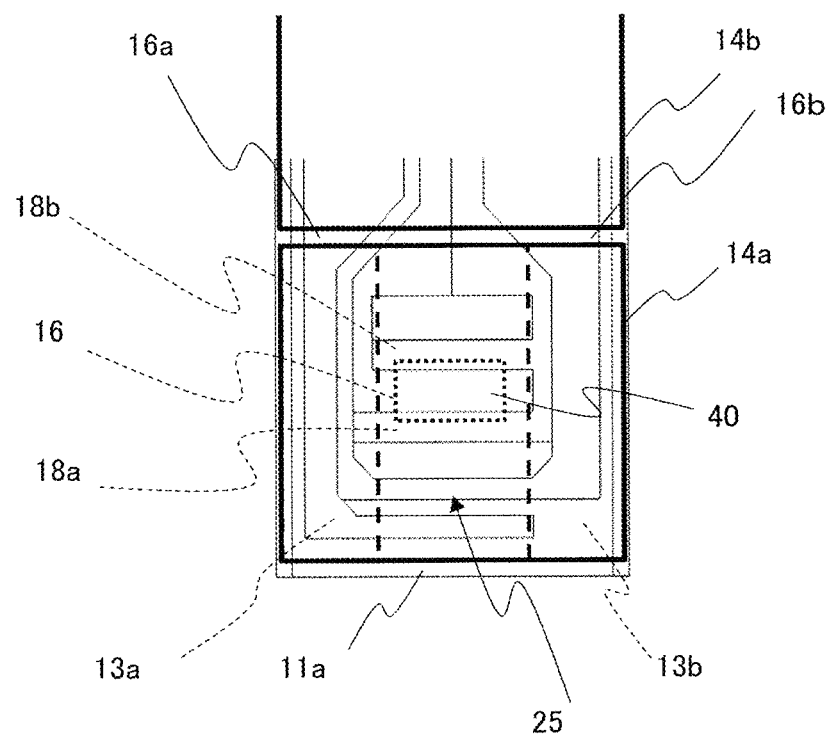
FIG. 4 is a diagram illustrating the production method for the biosensor, and illustrates that a spacer and a cover are provided on one end of the insulation substrate.

Next, the spacer 13a, the spacer 13b, and the reinforcing material 13c are stacked on the electrode layer 12. Further, the cover 14a and the cover 14b are stacked. As illustrated in FIG. 4, on the side of the one end 11a of the insulation substrate 11, the spacer 13a and the spacer 13b are disposed in parallel with each other in the longitudinal direction of the insulation substrate 11 such that the reagent layer 40 is placed between the spacer 13a and the spacer 13b. The reagent layer 40 is not in contact with or not covered by the spacer 13a and the spacer 13b. In addition, the reinforcing material 13c (not illustrated in FIG. 4) is disposed on the electrode layer 12 so as to have a certain space relative to each of the spacer 13a and the spacer 13b. The space between the reinforcing material 13c and the spacer 13a forms a groove 16a and the space between the reinforcing material 13c and the spacer 13b forms a groove 16b.

The cover 14a is formed into a rectangular shape. The length of one side of the cover 14a is almost equal to the length, in the length direction, of each of the spacer 13a and the spacer 13b. The length of another side of the cover 14a is equal or substantially equal (e.g., within 10, 8, 5, 3 or less % difference in length) to the length, in the width direction, of the insulation substrate 11. The cover 14a is disposed on the spacer 13a and the spacer 13b. The cover 14b is disposed so as to overlap with the reinforcing material 13c and to have a space relative to the cover 14a. As materials for the spacer 13a, the spacer 13b, and the reinforcing material 13c, double-stick tapes may be used, for example. In this case, the spacer 13a, the spacer 13b, and the reinforcing material 13c serve as adhesives for attaching the cover 14a and the cover 14b to the substrate. In addition, the respective thicknesses of the spacer 13a, the spacer 13b, and the reinforcing material 13c may be easily made equal to one another.

As a result of attachment of the cover 14a onto the spacer 13a and the spacer 13b, a liquid-sample flow path (capillary) 25 enclosed by the upper surface of the electrode layer 12 on which the reagent layer 40 is formed, the respective inner surfaces of the spacer 13a and the spacer 13b, and the inner surface of the cover 14a, is formed. The capillary 25 has an opening on the one end 11a side and an opening on the opposite side thereto. The opening on the opposite side is connected to the groove 16a, the groove 16b, and the space between the cover 14a and the cover 14b.

The opening in the one end 11a side functions as an introduction port for a liquid sample (for example, blood) to be spotted onto the biosensor 10. The liquid sample is sucked into the capillary 25 through the introduction port by capillary phenomenon. As a result of flowing-in of the liquid sample, air in the capillary 25 is discharged through the groove 16a, the groove 16b, and the space between the cover 14a and the cover 14b. The cover 14a may be formed from a transparent resin material. When the cover 14a is transparent, the status of the sample introduced into the capillary 25 is visible.

Reagent Layer

Next, the reagent layer 40 applicable to the biosensor of the embodiment is described. The reagent layer 40 contains an oxidoreductase and an electron transfer mediator. For example, the electron transfer mediator may become a reduction type through a reaction between the oxidoreductase and substance to be measured (described below), may be electrochemically oxidized, and may be detected by oxidation current. A conventionally known electron transfer mediator may be used.

Specifically, for example, potassium ferricyanide, p-benzoquinone and a derivative thereof, phenazine methosulfate, indophenol, an indophenol derivative such as 2,6-dichloroindophenol, potassium β-naphthoquinone-4-sulfonate, ferrocene, a ferrocene derivative such as ferrocenecarboxylic acid, an osmium complex, a ruthenium complex, $NAD^+$, $NADP^+$, pyrroloquinoline quinone (PQQ), methylene blue, cytochrome c, cytochrome b, a copper complex, or the like may be used as the electron transfer mediator. Among the above mediators, potassium ferricyanide, ferrocene, an osmium complex, a ruthenium complex, $NAD^+$, $NADP^+$, or the like may be used.

Furthermore, for example, 1,1'-dimethyl-4,4'-bipyridinium salt, 1,1'-dibenzyl-4,4'-bipyridinium salt, 1,4-diaminobenzene, 2-methyl-1,4-naphthoquinone, N-methylphenazinium salt, 1-hydroxy-5-methylphenazinium salt, 1-methoxy-5-methylphenazinium salt, 9-dimethylaminobenzo-α-phenoxazin-7-ium salt, hexacyanoferrate(II) salt, 7-hydroxy-3H-phenoxazin-3-one 10-oxide, 3,7-diamino-5-phenylphenazinium salt, 3-(diethylamino)-7-amino-5-phenylphenazinium salt, 1,4-benzenediol, 1,4-dihydroxy-2,3,5-trimethylbenzene, N,N,N',N'-tetramethyl-1,4-benzenediamine, Δ2,2'-bi-1,3-dithiol, 2,6-dimethylbenzoquinone, 2,5-dimethylbenzoquinone, 2,3,5,6-tetramethyl-2,5-cyclohexadiene-1,4-dione, 2,6-dichloro-4-[(4-hydroxyphenyl)imino]-2,5-cyclohexadien-1-one, 2,6-dichloro-4-[(3-chloro-4-hydroxyphenyl)imino]-2,5-cyclohexadien-1-one, 7-(diethylamino)-3-imino-8-methyl-3H-phenoxazine salt, 3,7-bis(dimethylamino)phenothiazin-5-ium salt, or the like may be used as the mediator.

The oxidoreductase is not particularly limited as long as an oxidation-reduction reaction of the oxidoreductase is caused with a substance to be measured and the electron transfer mediator which are contained in a sample. The oxidoreductase may be determined, as appropriate, according to the kind of the substance to be measured, etc.

Specifically, examples of the oxidoreductase include glucose oxidase (GOD), pyranose oxidase, glucose dehydrogenase (GDH), lactate oxidase, lactate dehydrogenase, fructose dehydrogenase, galactose oxidase, cholesterol oxidase, cholesterol dehydrogenase, alcohol oxidase, alcohol dehydrogenase, pyruvate oxidase, glucose-6-phosphate dehydrogenase, amino-acid dehydrogenase, formate dehydrogenase, glycerol dehydrogenase, acyl-CoA oxidase, choline oxidase, 4-hydroxybenzoate hydroxylase, maleate dehydrogenase, sarcosine oxidase, and uricase.

A combination of the oxidoreductase and the mediator is not limited to a particular combination. However, examples of such a combination include a combination of GOD and potassium ferricyanide, a combination of GDH and a ruthenium complex, a combination of cholesterol dehydrogenase and ferrocene, and a combination of alcohol dehydrogenase and a copper complex.

A biosensor unit including a plurality of the biosensors each having the aforementioned configuration may be formed. In this case, the biosensor unit is formed such that enzymes in the reagent layers in the respective biosensors have the same reaction speed and that the areas of the hydrophilic regions in the respective biosensors are substantially equal to one another. The "reaction speed" is determined based on a time course, the sensitivity in amperometry measurement, or a measurement time, for example. The expression "substantially equal" means that the error of the area of the hydrophilic region in each biosensor is equal to or smaller than 10% of a predetermined area (a specified value (also referred to as "theoretical value")) that is specified. However, the error range may be set to be equal to or smaller than 5%, or be equal to or smaller than 1%.

Measurement Apparatus

Figure 5:
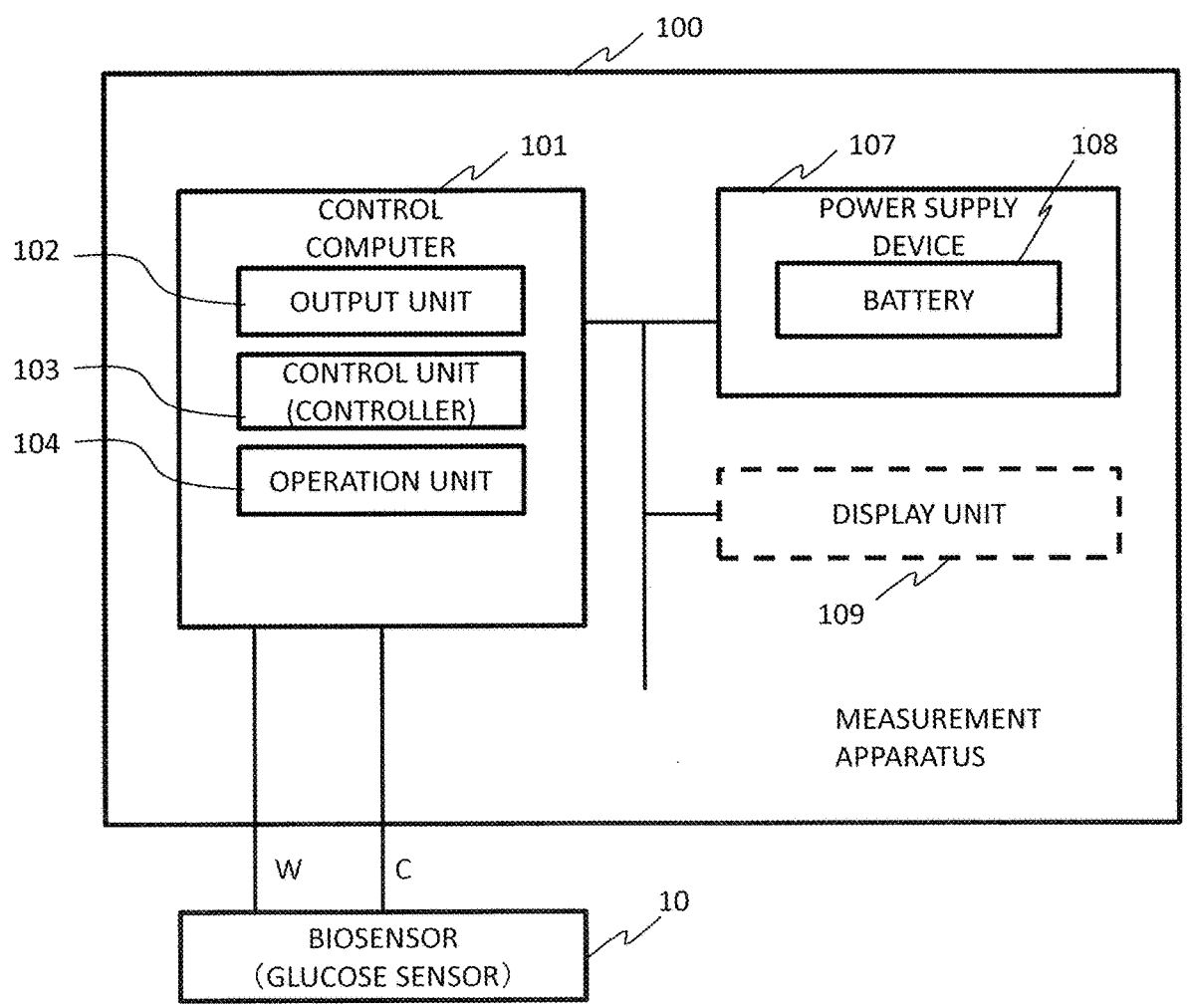
FIG. 5 illustrates a configuration example of a measurement apparatus.

Next, a measurement apparatus for measuring the concentration of substance to be measured using the biosensor 10 is described with reference to FIGS. 5 and 6. FIG. 5 illustrates the configuration example of the measurement apparatus. In FIG. 5, a measurement apparatus 100 is a glucose measurement apparatus that measures a glucose (blood sugar) concentration by using the biosensor 10 which is a glucose sensor. However, the configuration of the measurement apparatus 100 described below is an example, and the configuration of the measurement apparatus is not limited to the aspect illustrated in FIG. 5.

In the example illustrated in FIG. 5, a control computer 101 and a power supply device 107 are provided on a substrate (not illustrated) that is housed in a casing. The control computer 101 includes, as the hardware thereof, a processor such as a CPU (central processing unit), a recording medium such as a memory (for example, a RAM (random access memory) or a ROM (read only memory)), and a communication unit.

The processor loads a program stored in the recording medium (for example, the ROM), into the RAM and executes the program. Accordingly, the control computer 101 functions as a device including an output unit 102, a control unit 103, and an operation unit 104. The control computer 101 may include an auxiliary storage device such as a semiconductor memory (an EEPROM, a flash memory) and a hard disk.

The control unit 103 controls a timing for voltage application, the value of voltage to be applied, and the like. The power supply device 107 includes a battery 108, and supplies power for operation to the control computer 101, etc. The power supply device 107 may be disposed outside the casing.

The control unit 103 applies a predetermined voltage to between the counter electrode and the working electrode of the biosensor 10 by using a terminal W and a terminal C which correspond to the working electrode and the counter electrode, respectively. The control unit 103 measures response current obtained at the terminal W from the working electrode, and sends the measurement result of the response current to the operation unit 104.

The operation unit 104 calculates the concentration of substance (glucose) to be measured, based on the detected current value, and stores the calculated concentration. The output unit 102 performs data communication with a display unit 109, to transmit, to the display unit 109, a calculation result of the concentration of substance (glucose) to be measured, which has been calculated by the operation unit 104. The display unit 109 may display, in a predetermined format on a display screen thereof, the calculation result of a glucose concentration received from the measurement apparatus 100, for example.

Figure 6:
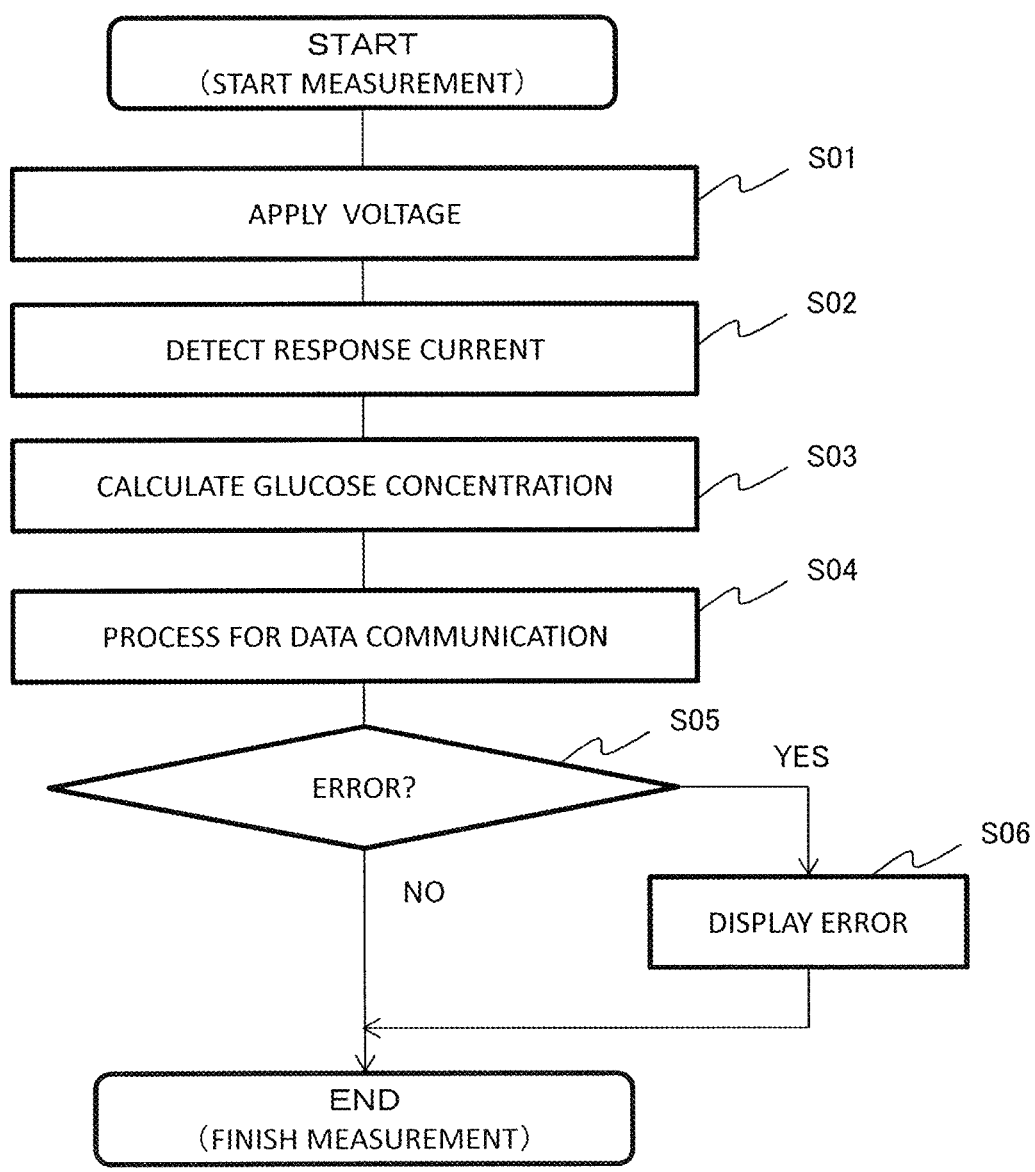
FIG. 6 is a flowchart of a processing example in the measurement apparatus.

FIG. 6 is a flowchart indicating an example of processes to be performed by the measurement apparatus (glucose-concentration measurement processes to be performed by the control computer 101). The CPU (the control unit (controller) 103) of the control computer 101 receives an instruction for starting measurement of a glucose concentration. The control unit 103 applies a predetermined voltage to the biosensor 10 (step S01), and starts to measure a response current from the biosensor 10 (step S02). Detection of attachment of the biosensor 10 to the measurement apparatus 100 may be used as an instruction to start concentration measurement.

The operation unit 104 calculates a glucose concentration based on the response current value (step S03). For example, the control computer 101 holds in advance a formula for calculating a glucose concentration corresponding to a response current value or the calibration curve data of a glucose concentration, and the operation unit 104 calculates the glucose concentration by using the formula or the calibration curve.

The output unit 102 transmits the calculation result of the glucose concentration to the display unit 109 over a communication link formed between the output unit 102 and the display unit 109 (step S04). Thereafter, the control unit 103 determines the presence/absence of a measurement error (step S05). When the error has not occurred, the measurement is ended. When the error has occurred, an error display is performed and the processes of the flowchart illustrated in FIG. 6 is ended.

Experiment 1

Example 1

In Example 1 of the biosensor according to the embodiment, a biosensor having the structure is produced by the method as described with reference to FIGS. 1, 2, 3A to 3D. In Example 1, the aforementioned hydrophilic region 31 and the aforementioned surrounding region 32 are formed, a reagent liquid is dispensed onto the hydrophilic region 31 and is solidified, so that the reagent layer 40 is formed on the hydrophilic region 31. The reagent liquid is prescribed as follows. The dispensing amount (the supply amount) is 0.25 µL.

Prescription of Reagent
Smectite solution: 89.2 µg
Purified water: 124.9 µg
Hexaamineruthenium chloride [Ru(NH3)6Cl3] (mediator): 6.1 µg
Sucrose laurate solution: 12.0 µg
GOD (enzyme): 17.8 µg Comparative Example 1

In Comparative Example 1, the biosensor in which the hydrophilic region 31 is not formed (surface treatment (hydrophilization) is not performed) is produced. The structure of Comparative Example 1 is identical to that of Example 1, except that the step for forming the hydrophilic region 31 is omitted (the hydrophilic region 31 is not included). The reagent liquid the amount of which is the same (0.25 µL) as that in Example 1 and which had been prescribed in the same manner as in Example 1, is dispensed.

Figure 7A:
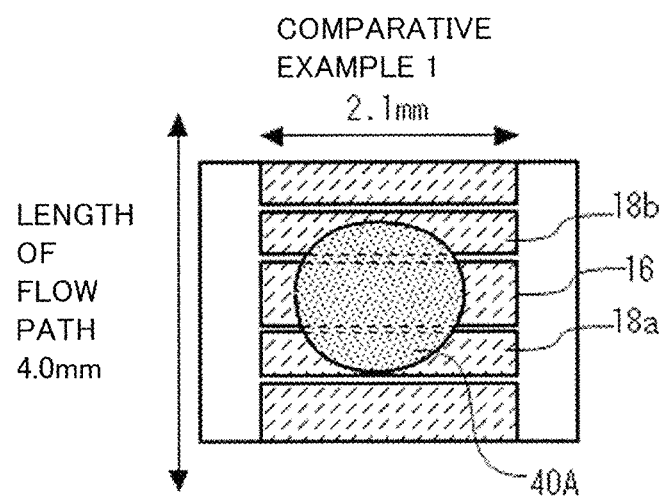
FIG. 7A illustrates the reagent layer of the biosensor of Comparative Example 1.
Figure 7B:
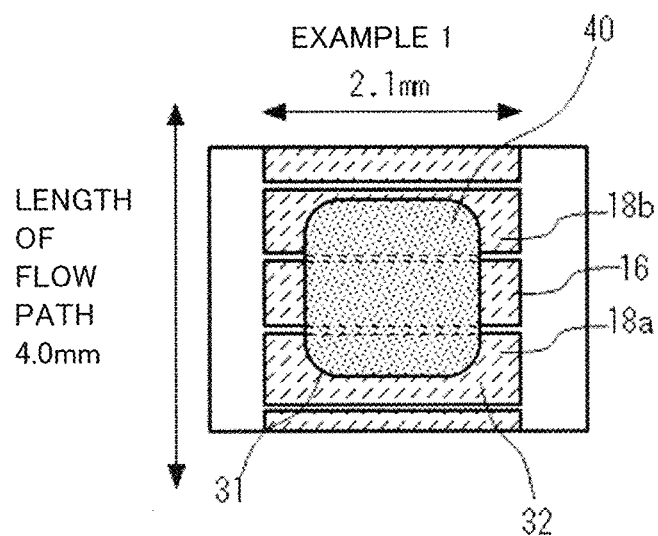
FIG. 7B illustrates the reagent layer of the biosensor of Example 1.

FIG. 7A illustrates a reagent layer 40A in the biosensor of Comparative Example 1, and FIG. 7B illustrates the reagent layer 40 in the biosensor of Example 1. As illustrated in FIG. 7A, since hydrophilization by surface treatment is not performed in Comparative Example 1, the dropped reagent did not spread and the outer edge shape (circular shape) of the reagent layer 40 at the time of dispensing is kept. In contrast, as illustrated in FIG. 7B, the reagent layer 40 spread over the entire hydrophilic region 31 in Example 1.

Chronoamperometry Measurement

The electrode response characteristics of the glucose sensors of Example 1 and Comparative Example 1 are evaluated by chronoamperometry measurement. Chronoamperometry measurement is performed in such a way that whole blood having a predetermined concentration is introduced into the sample introduction port of the biosensor (glucose sensor) 10, voltage at 200 mV is applied for 5.8 secs (open circuit: 1.0 sec), and the current value after 6.8 secs from start of measurement is read out.

In Example 1, the experiment is performed for blood sugar concentrations in whole blood of 67 mg/dL, 134 mg/dL, 336 mg/dL, and 600 mg/dL. Also in Comparative Example 1, measurement is performed for blood sugar concentrations of 67 mg/dL, 134 mg/dL, 336 mg/dL, and 600 mg/dL.

Figure 8A:
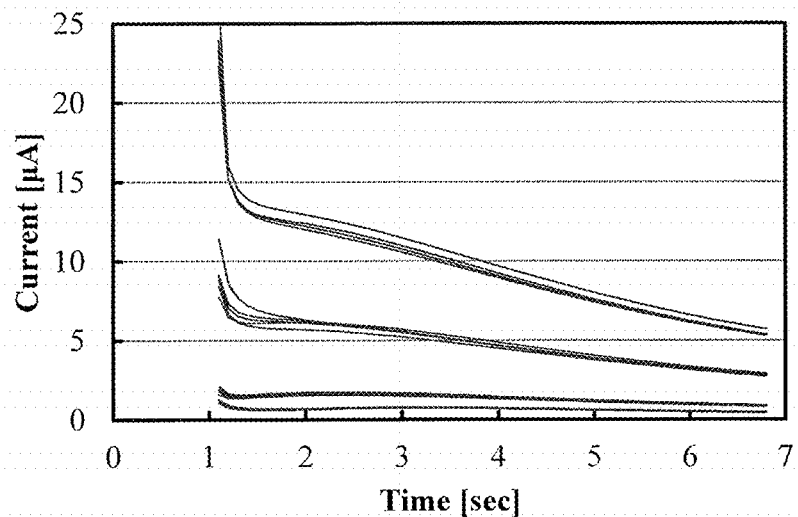
FIG. 8A indicates a measurement result in Comparative Example 1 (in which a hydrophilic region is not formed).
Figure 8B:
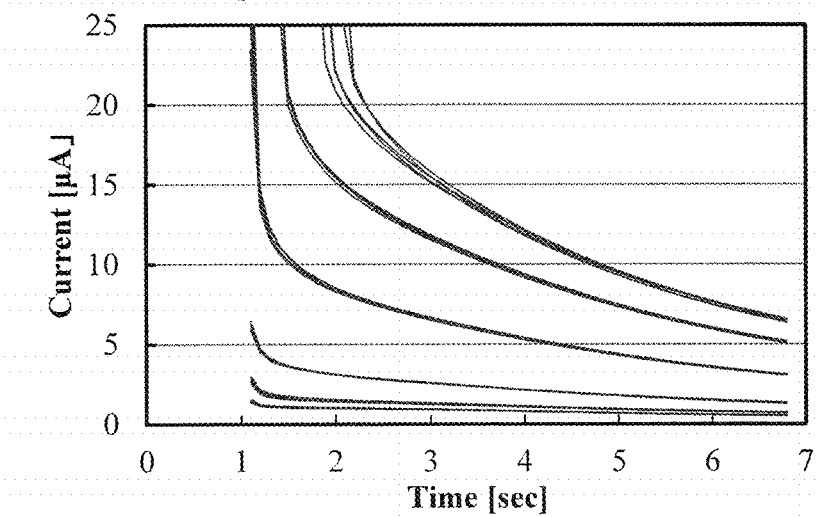
FIG. 8B indicates a measurement result in Example 1 (in which the hydrophilic region is formed).

FIG. 8A indicates a measurement result in Comparative Example 1 (in which the hydrophilic region 31 is not provided). FIG. 8B indicates a measurement result of Example 1 (in which the hydrophilic region 31 is provided). As indicated in FIG. 8A, the hydrophilic region 31 is not formed (surface treatment is not performed) in Comparative Example 1. Accordingly, compared to Example 1, the shape of the reagent layer 40A and the contact area of the reagent layer 40A with the working electrode 16 and the contact area of the reagent layer 40A with the counter electrode 18 are unstable among the individual sensors. As a result, it is considered that the diffused states of the reagent to be dissolved by samples are different from one another among the sensors, thus, variation in waveform in initial response occurred. In addition, since the contact areas of the reagents with the electrode layers are unstable among the individual sensors, variation in waveform at an endpoint occurred.

In contrast, in Example 1, since the hydrophilic region 31 is formed (surface treatment was performed), the shape and the contact area of the reagent layer 40 formed on the working electrode 16 and the counter electrode 18 are stable. As a result, the diffused states of the reagent to be dissolved by samples are more uniform, compared with Comparative Example 1, and variation in waveform in initial response is suppressed. In addition, since the contact areas of the reagents with the electrode layers are stable among the individual sensors, variation in waveform at an endpoint is suppressed.

Figure 9:
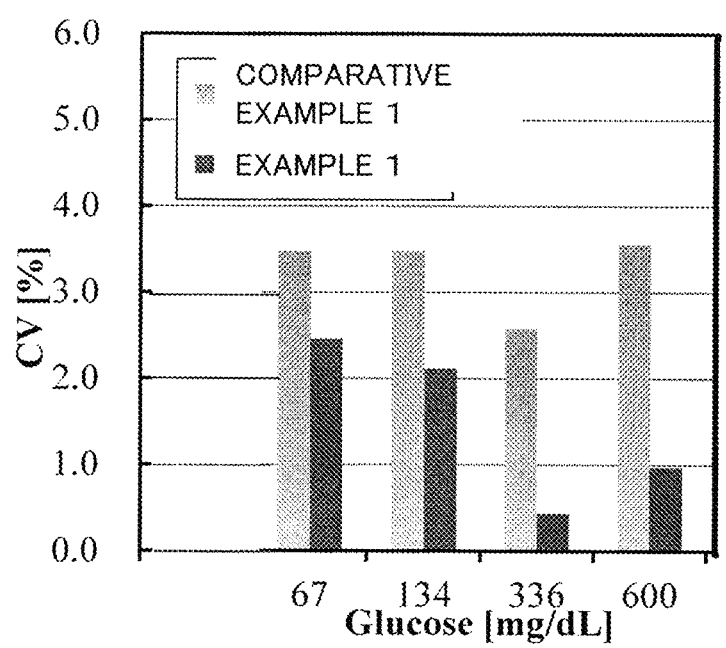
FIG. 9 indicates evaluation results of CV values (simultaneous reproductivity) based on measurement values obtained after 6.8 seconds from start of application of voltage, in Comparative Example 1 and Example 1.

Table 1 and FIG. 9 indicate the evaluation result of CV values (simultaneous reproductivity) based on the measurement values 6.8 seconds after start of measurement in Comparative Example 1 and Example 1.

TABLE 1

| Glucose concentration (mg/dl) | Comparative Example 1 | Example 1 |
|---|---|---|
| 45 | — | 2.87% |
| 67 | 3.48% | 2.46% |
| 134 | 3.48% | 2.12% |
| 336 | 2.58% | 0.44% |
| 600 | 3.56% | 0.97% |
| 800 | — | 1.37% |

In Example 1, the diffusion range of the reagent liquid is defined, and thus, the contact area of the reagent layer with the working electrode and the contact area of the reagent layer with the counter electrode are defined. Accordingly, as is clear from Table 1 and FIG. 9, the more preferable CV value (simultaneous reproductivity) is obtained, compared with Comparative Example 1 in which the diffusion range of the reagent liquid is not limited. That is, variation in measurement values among individual biosensors is suppressed, and the accuracy is improved.

Experiment 2

Next, in Experiment 2, a plurality of biosensors of which the degrees of surface modification are different from one another are prepared, the reagent liquids (the supply amount: 0.25 μL) predetermined in the same manner as in Example 1 are used, and the contact angles of the reagents and the diffusion of the reagents are checked. FIGS. 10A to 10G indicate the results of Experiment 2.

Figure 10A:
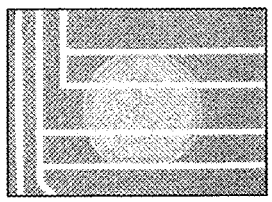
FIGS. 10A to 10G illustrate a result of Experiment 2.
Figure 10E:
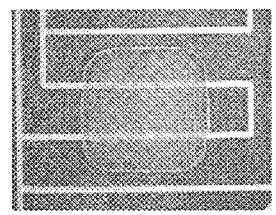
Figure 10B:
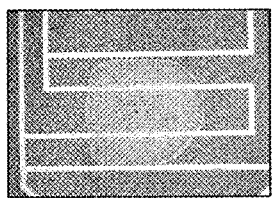
Figure 10F:
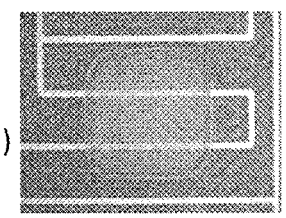
Figure 10C:
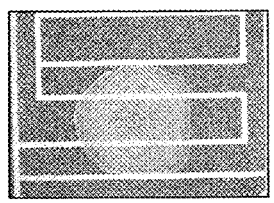
Figure 10G:
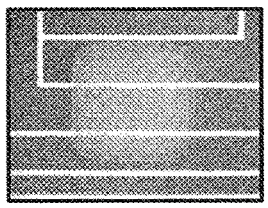
Figure 10D:
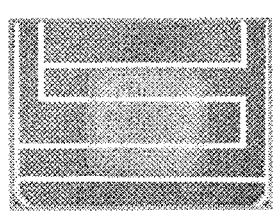

As indicated in FIG. 10A, in the case where surface treatment is not performed (the hydrophilic region 31 is not formed), the contact angle θ of the reagent liquid is 83.6°. FIGS. 10B to 10G each indicate the contact angle θ when the degree of surface modification is changed, the difference Δθ from the contact angle θ of 83.6° which is obtained when surface treatment is not performed, and the outer edge shape of the reagent layer. The outer edge shapes of the hydrophilic regions 31 are rectangular shapes.

According to the result of Experiment 2, when Δθ is 40° or larger, a rate at which the reagent layer 40 is obtained by solidification of a reagent liquid spread over the entire hydrophilic region 31 exceeded, for example, 70 percent. When Δθ is 60° or larger, a rate at which the reagent layer 40 is obtained by solidification of a reagent liquid spread over the entire hydrophilic region 31 exceeded, for example, 90 percent. Therefore, the difference (Δθ) between the contact angle relative to the hydrophilic region 31 and the contact angle relative to the surrounding region 32 may be 40°, 50°, or 60° or larger.

Experiment 3

Comparative Example 2

Figure 11:
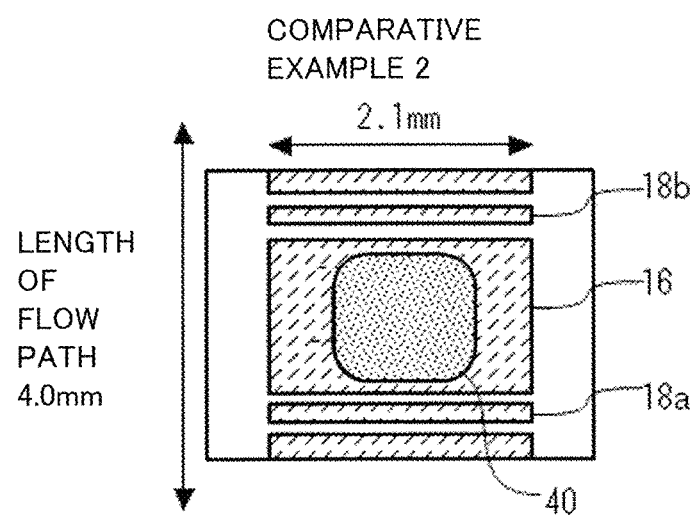
FIG. 11 is a diagram illustrating Comparative Example 2.

In Comparative Example 2, as illustrated in FIG. 11, a biosensor having the reagent layer 40 formed on the working electrode 16 is produced by forming the hydrophilic region 31 on the working electrode 16, in the part including the working electrode 16 and the counter electrode 18. The reagent liquid for forming the reagent layer 40 is prescribed in the same manner as in Example 1 and the same amount of the reagent liquid is dispensed as that in Example 1.

Figure 12:
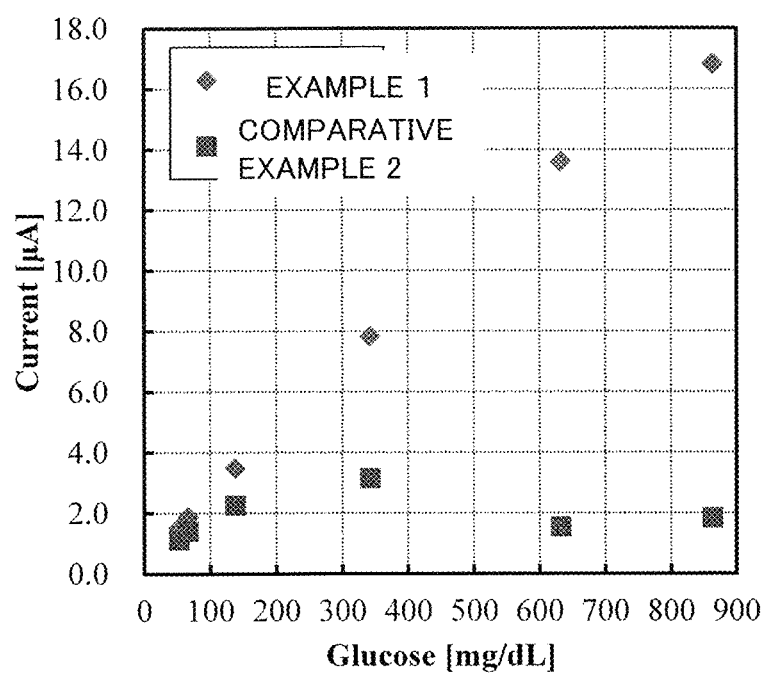
FIG. 12 is a graph indicating the relationship between the responsive current in the biosensor and the glucose concentration in Example 1, and the relationship between the responsive current in the biosensor and the glucose concentration in Comparative Example 2.

FIG. 12 is a graph indicating the relationship between the response current and the glucose concentration in the biosensor of Example 1, and the relationship between the response current and the glucose concentration in the biosensor of Comparative Example 2.

As is clear from FIG. 12, the glucose concentrations corresponding to the response current values are measured in Example 1, whereas the detected current values do not depend on the glucose concentrations but are approximately 2 μA in Comparative Example 2. Accordingly, it is understood that in the biosensor having the reagent layer 40 containing an oxidoreductase and a mediator, a glucose concentration is not preferably measured unless the reagent layer 40 is formed on the working electrode 16 and the counter electrode 18.

In the aforementioned embodiment, as illustrated in FIG. 3, the hydrophilicity of a portion, on the substrate surface, exposed from the opening 21 is increased, whereby the hydrophilic region 31 is formed. Alternatively, a portion exposed from the opening 21 may be formed as the hydrophilic region 31 having relative hydrophilicity by imparting hydrophobicity (water repellency) to the surrounding of the portion, for example.

Configuration of Electrode Section

The configuration of the electrode layer 12 and the hydrophilic region 31 of the biosensor 10 according to the embodiment is described in detail below. FIG. 13 is a diagram of the electrode section and a hydrophilic region in the biosensor 10. In the embodiment, the electrode layer 12 includes the counter electrode 18a, the counter electrode 18b, and the working electrode 16 arranged in the first direction (the longitudinal direction of the biosensor 10).

The working electrode 16 is disposed in parallel with the counter electrode 18a and the counter electrode 18b while being sandwiched between the counter electrode 18a and the counter electrode 18b. That is, the length of a space separating the working electrode 16 from the counter electrode 18a is equal to that of a space separating the working electrode 16 from the counter electrode 18b.

As illustrated in FIG. 13, respective ends, in the second direction (the width direction of the biosensor 10) orthogonal to the first direction, of the working electrode 16, the counter electrode 18a and the counter electrode 18b are defined by side surfaces of the spacer 13a and the spacer 13b placed on the electrode layer 12. Accordingly, the working electrode 16, the counter electrode 18a, and the counter electrode 18b between the spacer 13a and the spacer 13b are each formed into an oblong (a band-like rectangular shape). Moreover, the respective lengths of the counter electrode 18a and the counter electrode 18b are equal to each other in the first direction.

The hydrophilic region 31 is formed into a rectangular shape having sides in the length direction and sides in the width direction (however, corners of the rectangular shape may be rounded). The hydrophilic region 31 is formed such that the sides, in the length direction, of the hydrophilic region 31 extend in the first direction and the sides 31a, 31b in the width direction extend in the second direction. The surrounding region of the hydrophilic region 31 is formed in a low-hydrophilic region.

The length, in the width direction, of the hydrophilic region 31 may be shorter than a length between the spacer 13a and the spacer 13b, and the hydrophilic region 31 is formed between respective ends, in the second direction, of the working electrode 16, the counter electrode 18a, and the counter electrode 18b. Ends (the sides 31a, 31b extending in the second direction), in the first direction, of the hydrophilic region 31 are disposed so as to overlap with the electrodes surfaces of the electrodes (the counter electrode 18a, the counter electrode 18b) that are disposed on the outermost side in the first direction.

As a result of the aforementioned configuration of the working electrode 16, the counter electrode 18a, the counter electrode 18b, and the hydrophilic region 31, advantageous effects below may be obtained. FIGS. 14A to 14D are diagrams illustrating advantageous effects of the biosensor 10.

As illustrated in FIG. 13, for example, the hydrophilic region 31 is formed at a position such that the overlapping area thereof with the counter electrode 18a is substantially equal to the overlapping area thereof with the counter electrode 18b, and the hydrophilic region 31 is linearly symmetrical with a line bisecting, in the longitudinal direction, the biosensor 10. This position is defined as a reference position. Here, when the biosensor is produced, the formation position of the hydrophilic region 31 may be deviated from the reference point by an influence such as a mechanical error, slight vibration, a friction force during transport.

Figure 14A:
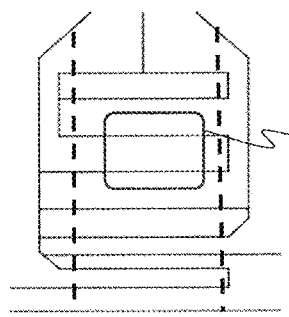
FIG. 14A illustrates that the formation position of the hydrophilic region is deviated from a reference position to the right side.
Figure 14B:
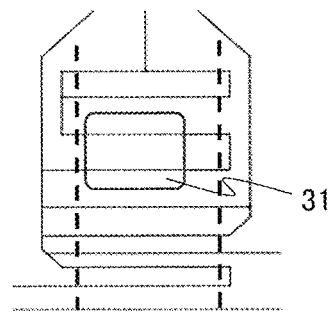
FIG. 14B illustrates that the formation position of the hydrophilic region is deviated from the reference position to the left side.

FIG. 14A illustrates a case where the formation position of the hydrophilic region 31 is deviated to right from the reference position. FIG. 14B illustrates a case where the formation position of the hydrophilic region 31 is deviated to left from the reference position. However, the working electrode 16, the counter electrode 18a, and the counter electrode 18b are disposed in parallel with one another, and the hydrophilic region 31 is formed between respective both ends, in the second direction (the width direction of the biosensor 10, in the present embodiment) orthogonal to the first direction, of the working electrode 16, the counter electrode 18a, and the counter electrode 18b (the hydrophilic region 31 does not include any end, in the second direction, of the working electrode 16, the counter electrode 18a, or the counter electrode 18b). Thus, even when the hydrophilic region 31 is deviated in any of the left, right, upper, and lower directions, the overlapping area of the hydrophilic region 31 with the working electrode 16 and the counter electrodes 18a, 18b is unchanged.

Figure 14C:
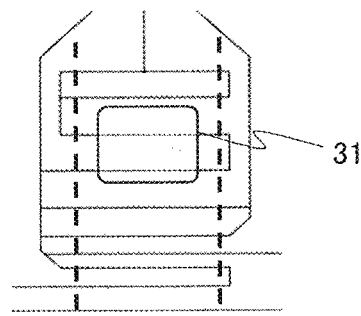
FIG. 14C illustrates that the formation position of the hydrophilic region is deviated from the reference position to the upper side.
Figure 14D:
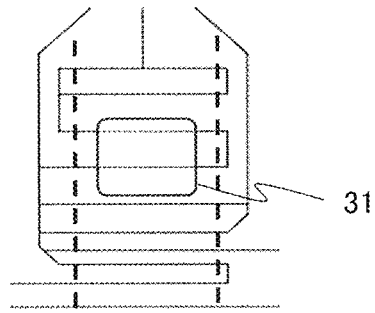
FIG. 14D illustrates the formation position of the hydrophilic region is deviated from the reference position to the lower side.

FIG. 14C illustrates a case where the formation position of the hydrophilic region 31 is deviated to the upper side (the another end 11b side of the insulation substrate 11; see FIG. 2) from the reference position. FIG. 14D illustrates a case where the formation position of the hydrophilic region 31 is deviated to the lower side (to the one end 11a side of the insulation substrate 11) from the reference position. In both cases, the overlapping area of the hydrophilic region 31 with the working electrode 16 is constant as long as an end (a side), of the hydrophilic region 31, on the one end 11a side is positioned on an electrode surface of the counter electrode 18a (positioned between edges) and an end (a side), of the hydrophilic region 31, on the another end 11b side is positioned on an electrode surface of the counter electrode 18b. Thus, the overlapping areas (the total value) of the counter electrode 18a and the counter electrode 18b with the hydrophilic region 31 are unchanged.

Therefore, even when the hydrophilic region 31 is formed to be deviated in any of the left, right, upper, and lower directions, the contact areas of the reagent layer 40 that is formed so as to fill the hydrophilic region 31, with the working electrode 16, the counter electrode 18a, and the counter electrode 18b are unchanged. Accordingly, variation in sensitivity due to variation in contact area among the biosensors 10 may be suppressed.

Experiment 4

Comparative Example 3

Figure 15A:
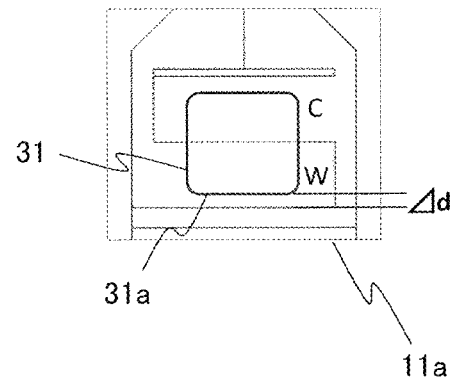
FIG. 15A is a diagram illustrating the biosensor of Comparative Example 3.

In Comparative Example 3, as illustrated in FIG. 15A, a biosensor is produced by forming the rectangular hydrophilic region 31 on an electrode having a two-electrode configuration including the working electrode W and the counter electrode C disposed parallel with each other, solidifying a reagent filling the entire hydrophilic region 31, and thereby forming a reagent layer. The reagent is prescribed in the same manner as in Example 1. A plurality of the biosensors are prepared so as to have the different distances Δd each of which is between the counter electrode W on the one end 11a side (the lower end) of the insulation substrate 11 and the side 31a, of the hydrophilic region 31, on the one end 11a side.

Example 2

Figure 15B:
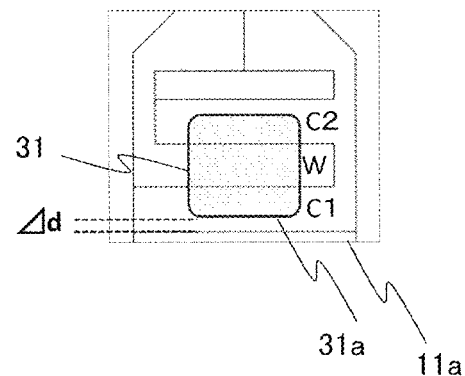
FIG. 15B is a diagram illustrating the biosensor of Example 2.
Figure 15C:
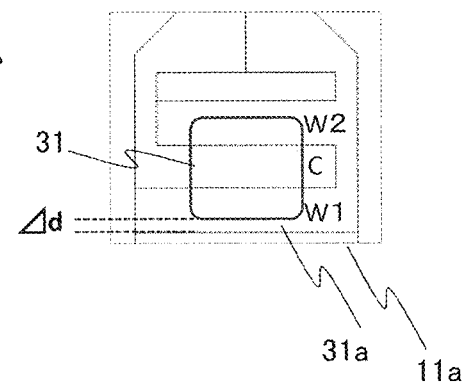
FIG. 15C is a diagram illustrating the biosensor of Example 3.

In Example 2, as illustrated in FIG. 15B, a biosensor is produced by forming the rectangular hydrophilic region 31 on an electrode having a two-electrode configuration in which the working electrode W is sandwiched by the counter electrodes C1 and C2 which are parallel with the working electrode W, solidifying a reagent filling the entire hydrophilic region 31, and thereby forming a reagent layer. The reagent is prescribed in the same manner as in Example 1. A plurality of the biosensors are prepared so as to have the different distances Δd each of which is between the counter electrode C1 on the one end 11a side of the insulation substrate 11 and a side, of the hydrophilic region 31, on the one end 11a side.

Example 3

In Example 3, as illustrated in FIG. 15B, a biosensor is produced by forming the rectangular hydrophilic region 31 on an electrode having a two-electrode configuration in which the counter electrode C is sandwiched by the working electrodes W1 and W2 which are parallel with the counter electrode C, solidifying a regent filling the entire of the hydrophilic region 31, and thereby, forming a reagent layer. The reagent is prescribed in the same manner as in Example 1. A plurality of biosensors having different distances Δd each of which are between the one end 11a side (the lower side end) of the working electrode W1 and a side, of the hydrophilic region, on the one end 11a side, are prepared.

Chronoamperometry Measurement

In Comparative Example 3 and Examples 2 and 3, electrode response characteristics of the respective glucose sensors are evaluated by chronoamperometry measurement. The same chronoamperometry measurement as that in Example 1 is adopted.

Figure 16A:
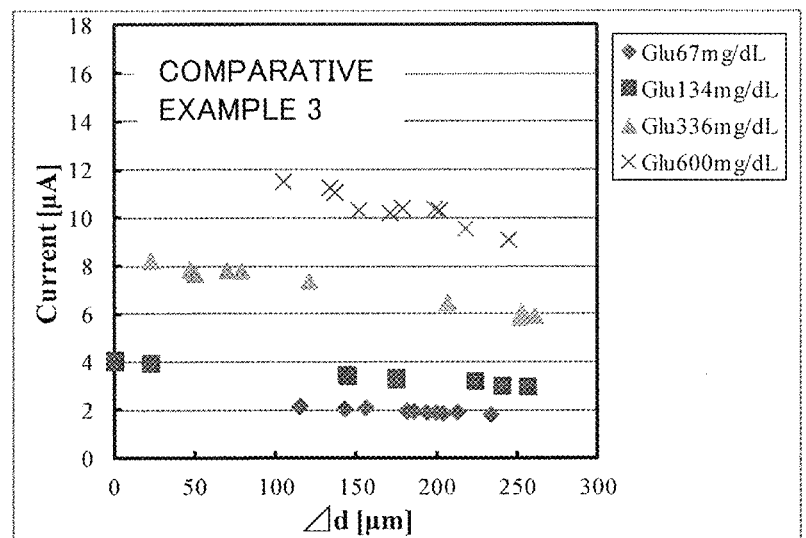
FIG. 16A indicates a measurement result of Comparative Example 3 (in which the ratio between the working electrode and the counter electrode is 1:1).
Figure 16B:
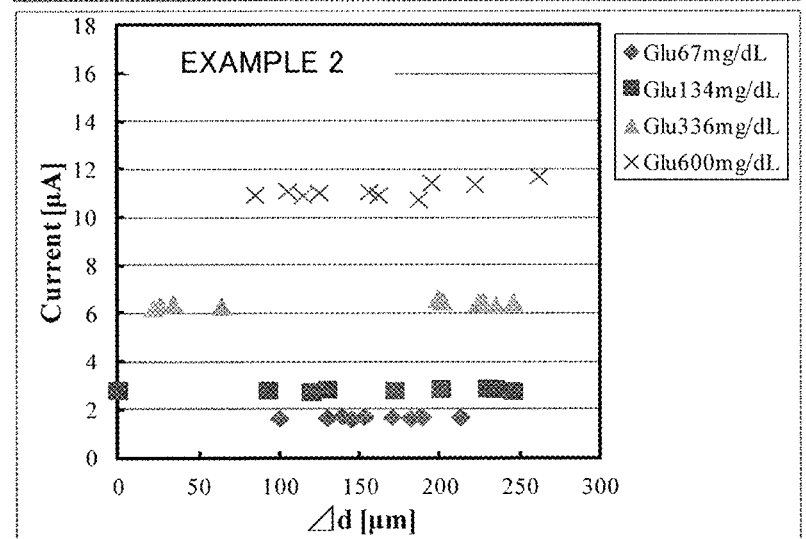
FIG. 16B indicates a measurement result of Example 2 (in which the electrode configuration is CWC).
Figure 16C:
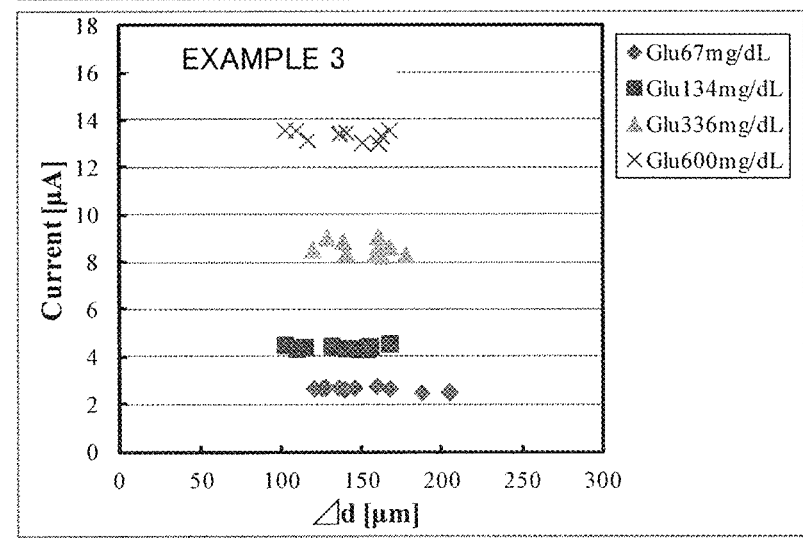
FIG. 16C indicates a measurement result of Example 3 (in which the electrode configuration is WCW).

FIG. 16A indicates a measurement result in Comparative Example 3 (having the configuration in which the ratio between the working electrode and the counter electrode is 1:1). FIG. 16B indicates a measurement result in Example 2 (having the electrode configuration of CWC). FIG. 16C indicates a measurement result in Example 3 (having the electrode configuration of WCW).

In Comparative Example 3, the ratio between the contact area between the working electrode and the reagent layer and the contact area between the counter electrode and the reagent layer is varied with variation in Δd. In contrast, in Examples 2 and 3, the ratio between the contact area between the working electrode and the reagent layer and the contact area between the counter electrode and the reagent layer is constant independently of variation in Δd.

As a result of this, in Comparative Example 3, variation in response current (the glucose concentration) occurred, as indicated in FIG. 16A. In contrast, in Examples 2 and 3, as indicated in FIGS. 16B and 16C, more stable response current (the glucose concentration) is obtained than that in Comparative Example 3. That is, variation in sensitivity among biosensors may be suppressed. In addition, as is clear from the measurement results of Examples 2 and 3, even with the configuration in which the counter electrode and the working electrode are reversed, a stable measurement result may be obtained independently of variation in Δd.

Table 2 and FIG. 7 each indicate evaluation results, in Comparative Example 3, Example 2, and Example 3, of CV values (simultaneous reproducibility) based on the measurement values obtained after 6.8 seconds from start of measurement.

TABLE 2

| Glucose (ml/dl) | Conporative Example 3 | | Example 2 | | Example 3 | |
|---|---|---|---|---|---|---|
| | Δd | Glucose CV | Δd | Glucose CV | Δd | Glucose CV |
| 67 | 19.5% | 7.8% | 20.9% | 3.9% | 18.6% | 5.3% |
| 134 | 70.9% | 16.0% | 63.9% | 2.0% | 16.2% | 2.7% |
| 336 | 71.3% | 17.9% | 65.9% | 2.1% | 12.3% | 4.9% |
| 600 | 24.8% | 10.2% | 34.6% | 2.8% | 16.5% | 2.1% |

Figure 17:
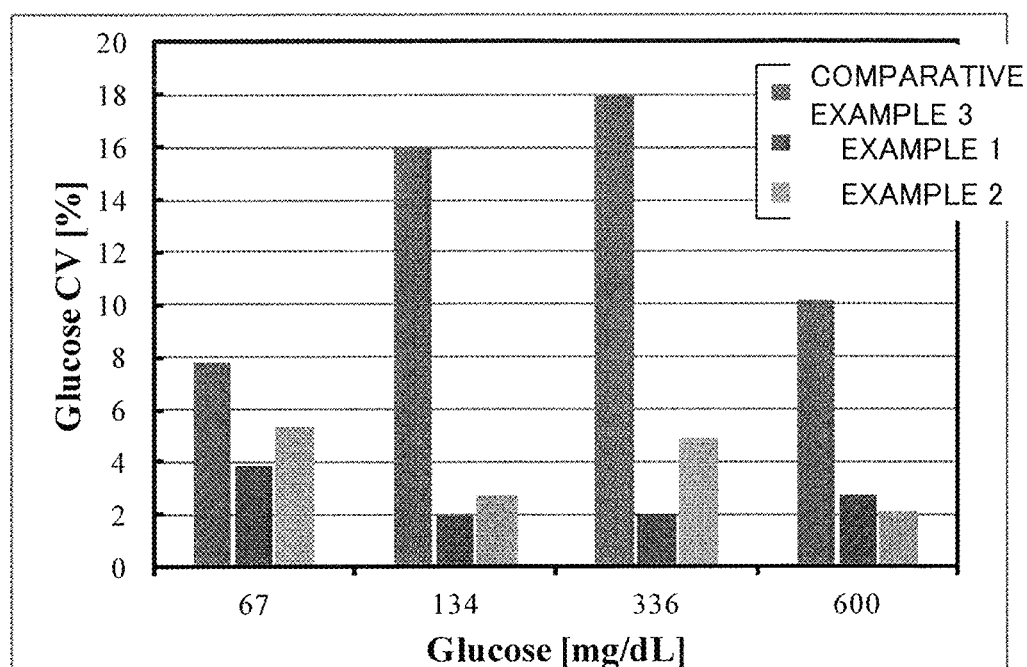
FIG. 17 is a graph indicating evaluation results of CV values (i.e., simultaneous reproductivity) based on measurement values after 6.8 seconds from start of the measurement in Comparative Example 3, Example 2, and Example 3.

In Examples 2 and 3, the contact area of the working electrode and the counter electrode with respect to the reagent layer is unchanged independently of variation in Δd. Accordingly, as is clear from Table 2 and FIG. 17, more suitable CV values (simultaneous reproductivity) are obtained, compared to those in Comparative Example 3 in which the ratio of the respective contact areas of the working electrode and the counter electrode with respect to the reagent layer is varied with variation in Δd. That is, variation in measurement value among individual biosensors is suppressed, and the accuracy is improved.

The configuration of the electrodes and the hydrophilic region having been described in the embodiment may be modified as follows. For example, the number of electrodes disposed in parallel with one another may be not three but five, seven, nine, eleven, or the like. Further, the two electrodes disposed on the outermost side in the first direction may be counter electrodes or may be working electrodes. The two electrodes disposed on the outermost side have the same length in the first direction. Moreover, it is preferable that, among electrodes disposed between the two electrodes on the outermost side, two electrodes, which are disposed so as to sandwich one or a plurality of electrodes, have the same length in the first direction.

Moreover, the example in which the hydrophilic region 31 (the reagent layer 40) has a rectangular shape has been described in the embodiment. However, the hydrophilic region 31 (the reagent layer 40) may have a circular shape or an ellipse shape. When the hydrophilic region 31 (the reagent layer 40) has an ellipse shape, one of the long axis and the short axis thereof is in the first direction and the other axis is in the second direction. However, when the hydrophilic region 31 (the reagent layer 40) has a rectangular shape, a limited space may be effectively utilized. That is, the rectangular shape is most suitable because the rectangular shape enables the sensitivity to be fully increased with a saved space.

Further, the configuration of the hydrophilic region (reagent layer) having been described in the embodiment is also applicable to a case where the working electrode and the counter electrode are disposed side by side in the width direction of the biosensor 10. In this case, the width direction of the biosensor 10 is "the first direction," and the longitudinal direction of the biosensor 10 is "the second direction orthogonal to the first direction." The configurations having been described in the embodiment may be combined, as appropriate, within the scope of the object of the invention.

What is claimed is:

1. A biosensor comprising:
    an insulation substrate;
    electrodes that are formed on the insulation substrate, the electrodes including a working electrode with two opposite ends and a counter electrode with two opposite ends, wherein said electrodes are disposed side by side in a first direction;
    a continuous hydrophilic layer having higher hydrophilicity than a surrounding region thereof, comprising first ends, in a second direction orthogonal to the first direction, between said two opposite ends of the working electrode and between said two opposite ends of the counter electrode, and comprising second ends, in the first direction, disposed on a pair of working electrodes or a pair of counter electrodes; and
    a reagent layer on the hydrophilic layer, the reagent layer comprising an enzyme and a mediator.
2. The biosensor according to claim 1, wherein the reagent layer has a rectangular shape.
3. The biosensor according to claim 1, wherein the distance between each of the pair of working electrodes or each of the pair of counter electrodes, and working electrodes or counter electrodes facing each of the pair of working electrodes or the pair of counter electrodes is the same.

4. The biosensor according to claim 1, wherein the working electrode and the counter electrode are in parallel with each other.

5. The biosensor according to claim 1, wherein not more than one continuous hydrophilic layer is formed on the working electrode or counter electrode.

6. The biosensor according to claim 1, wherein
the working electrode has a neighboring region without an counter electrode, and/or
the working electrode or the counter electrode is only partially covered with the reagent layer.

7. The biosensor according to claim 1, wherein the hydrophilic layer covers at least a part of the working electrode and at last two separate parts of the counter electrode.

8. The biosensor according to claim 1, wherein a single continuous hydrophilic layer is formed on the electrodes.

9. The biosensor according to claim 1, further comprising a spacer and a reinforcing material on the electrodes.

10. The biosensor according to claim 9, wherein the hydrophilic layer is not in direct contact with the spacer.

11. A production method for biosensor, the method comprising:
forming, on an insulation substrate, electrodes including a working electrode with two opposite ends and a counter electrode with two opposite ends, wherein said electrodes are arranged side by side in a first direction;
forming a continuous hydrophilic layer on the electrodes, the hydrophilic layer (i) having higher hydrophilicity than a surrounding region thereof, (ii) comprising first ends, in a second direction orthogonal to the first direction, disposed between said two opposite ends of the working electrode and between said two opposite ends of the counter electrode, and (iii) comprising second ends, in the first direction, a pair of working electrodes or a pair of counter electrodes;
supplying, to the continuous hydrophilic layer, a reagent liquid comprising an enzyme and a mediator; and
solidifying the reagent liquid to form a reagent layer.

12. The production method according to claim 11, wherein the reagent layer has a rectangular shape.

13. The production method according to claim 11, wherein the distance between each of the pair of working electrodes or each of the pair of counter electrodes, and working electrodes or counter electrodes facing each of the pair of working electrodes or the pair of counter electrodes is the same.

14. The production method according to claim 11, wherein the working electrode and the counter electrode are in parallel with each other.

15. The production method according to claim 11, wherein not more than one continuous hydrophilic layer is formed on the working electrode or counter electrode.

16. The production method according to claim 11, wherein
the working electrode has a neighboring region without an counter electrode, and/or
the working electrode or the counter electrode is only partially covered with the reagent layer.

17. The production method according to claim 11, wherein the hydrophilic layer covers at least a part of the working electrode and at last two separate parts of the counter electrode.

18. The production method according to claim 11, further comprising a spacer and a reinforcing material on the electrodes.

19. The production method according to claim 11, wherein the hydrophilic layer is not in direct contact with the spacer.

* * * * *